(12) United States Patent
Logunov et al.

(10) Patent No.: US 10,197,471 B2
(45) Date of Patent: Feb. 5, 2019

(54) METHODS AND DEVICES FOR MEASURING PROPERTIES OF COATINGS ON OPTICAL FIBERS

(71) Applicant: Corning Incorporated, Corning, NY (US)

(72) Inventors: Stephan Lvovich Logunov, Corning, NY (US); Kevin Alton Lewis, Montour Falls, NY (US)

(73) Assignee: Corning Incorporated, Corning, NY (US)

( * ) Notice: Subject to any disclaimer, the term of this patent is extended or adjusted under 35 U.S.C. 154(b) by 103 days.

(21) Appl. No.: 15/271,572

(22) Filed: Sep. 21, 2016

(65) Prior Publication Data

US 2017/0082535 A1  Mar. 23, 2017

Related U.S. Application Data

(60) Provisional application No. 62/221,382, filed on Sep. 21, 2015.

(51) Int. Cl.
  *G01M 11/00* (2006.01)
  *G01N 33/00* (2006.01)
  *G01M 11/08* (2006.01)

(52) U.S. Cl.
  CPC .......... *G01M 11/37* (2013.01); *G01M 11/088* (2013.01); *G01N 33/00* (2013.01); *G01N 2033/0096* (2013.01)

(58) Field of Classification Search
  CPC .................................................. G01M 11/37
  (Continued)

(56) References Cited

U.S. PATENT DOCUMENTS 8,731,366 B2    5/2014  Wu et al.
9,188,754 B1 *  11/2015  Risch ................... G02B 6/4486
(Continued)

FOREIGN PATENT DOCUMENTS

WO    WO2014146676 A1 *  9/2014

OTHER PUBLICATIONS

Galindez-Jamioy and Lopez-Higuera; "Brillouin Distributed Fiber Sensors: An Overview and Applications"; Hindawi Publishing Corporation, Journal of Sensors, vol. 2012, pp. 17.
(Continued)

*Primary Examiner* — Tarifur Chowdhury
*Assistant Examiner* — Omar Nixon
(74) *Attorney, Agent, or Firm* — Svetlana Z. Short; Smit Kapadia

(57) ABSTRACT

A method for measuring a mechanical property of a coating on an optical fiber may include collecting Brillouin frequency shift data of the coating on the optical fiber, and determining the mechanical property of the coating by comparing the collected Brillouin frequency shift data with correlation data that may include a set of collected sample Brillouin frequency shift data and a set of collected sample mechanical property data of a plurality of sample materials. The sample materials may include a substantially identical sample composition including one or more curable polymers, be prepared with varying processing conditions, and have different mechanical property values. The coating on the optical fiber may include a material composition substantially identical to the sample materials composition. The set of collected sample Brillouin frequency shift data may be correlated with the set of collected sample mechanical property data to determine a quantitative relationship therebetween.

20 Claims, 7 Drawing Sheets

(58) Field of Classification Search
USPC ........................................................ 356/73.1
See application file for complete search history.

(56) References Cited

U.S. PATENT DOCUMENTS

| | | | | |
|---|---|---|---|---|
| 2001/0028776 | A1* | 10/2001 | Yamano | G02B 6/448 385/128 |
| 2003/0077059 | A1* | 4/2003 | Chien | C03C 25/106 385/128 |
| 2003/0103549 | A1* | 6/2003 | Chi | G01L 1/242 374/45 |
| 2007/0134305 | A1* | 6/2007 | Zilberman | A61K 9/0024 424/443 |
| 2011/0211788 | A1* | 9/2011 | Yamamoto | G02B 6/02019 385/28 |
| 2012/0302862 | A1* | 11/2012 | Yun | A61B 5/0075 600/398 |
| 2012/0313307 | A1* | 12/2012 | Cartwright | C08J 5/042 267/141 |
| 2012/0321270 | A1* | 12/2012 | Imai | C03C 25/106 385/141 |
| 2014/0268110 | A1* | 9/2014 | Hartog | G01D 5/35364 356/73.1 |
| 2014/0285793 | A1* | 9/2014 | Jaaskelainen | G01L 1/242 356/32 |
| 2014/0308015 | A1 | 10/2014 | Bookbinder et al. | |
| 2015/0277031 | A1* | 10/2015 | Bookbinder | G02B 6/02033 385/115 |

OTHER PUBLICATIONS

Mizuno and Nakamura; "Brillouin Scattering in Polymer Optical Fibers: Fundamental Propoerties and Potential Use in Sensors"; Polymers, 2011, vol. 3, pp. 886-898.

* cited by examiner

METHODS AND DEVICES FOR MEASURING PROPERTIES OF COATINGS ON OPTICAL FIBERS

This application claims the benefit of priority under 35 U.S.C. § 119 of U.S. Provisional Application Ser. No. 62/221,382 filed on Sep. 21, 2015, the content of which is relied upon and incorporated herein by reference in its entirety.

BACKGROUND

Technical Field

The present specification generally relates to methods of measuring properties of materials and, more specifically, to methods of measuring properties of coatings on optical fibers.

TECHNICAL BACKGROUND

Optical fibers may be coated with cured polymer compositions. Knowledge of properties of the coatings on optical fibers, as well as properties of the optical fiber itself, may assist to determine the quality of such components of the coated optical fiber. A need exists for methods and apparatuses for measuring properties of optical fibers and/or coatings applied thereto.

SUMMARY

In one embodiment, a method for measuring a mechanical property of a coating on an optical fiber may comprise collecting Brillouin frequency shift data of the coating on the optical fiber, and determining the mechanical property of the coating by comparing the collected Brillouin frequency shift data of the coating with correlation data. The correlation data may comprise a set of collected sample Brillouin frequency shift data of a plurality of sample materials, and a set of collected sample mechanical property data of the plurality of sample materials. Each of the sample materials may comprise a substantially identical sample composition comprising one or more curable polymers. At least a portion of the sample materials may be prepared with varying processing conditions and may have different values of the mechanical property. The coating on the optical fiber may comprise a material composition that is substantially identical to the sample composition of the sample materials. And the set of collected sample Brillouin frequency shift data may be correlated with the set of collected sample mechanical property data to determine a quantitative relationship therebetween.

According to another embodiment, a method for measuring a Young's modulus of a coating on an optical fiber may comprise collecting Brillouin frequency shift data of the coating on the optical fiber, and determining the Young's modulus of the coating by comparing the collected Brillouin frequency shift data of the coating with correlation data. The correlation data may comprise a set of collected sample Brillouin frequency shift data of a plurality of sample materials, and a set of collected sample Young's modulus data of the plurality of sample materials. Each of the sample materials may comprise a substantially identical sample composition comprising one or more curable polymers. At least a portion of the sample materials may be prepared with varying cure conditions and have different values of Young's modulus. The coating on the optical fiber may comprise a material composition that is substantially identical to the sample composition of the sample materials. And the set of collected sample Brillouin frequency shift data may be correlated with the set of collected sample Young's modulus data to determine a quantitative relationship therebetween.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1:
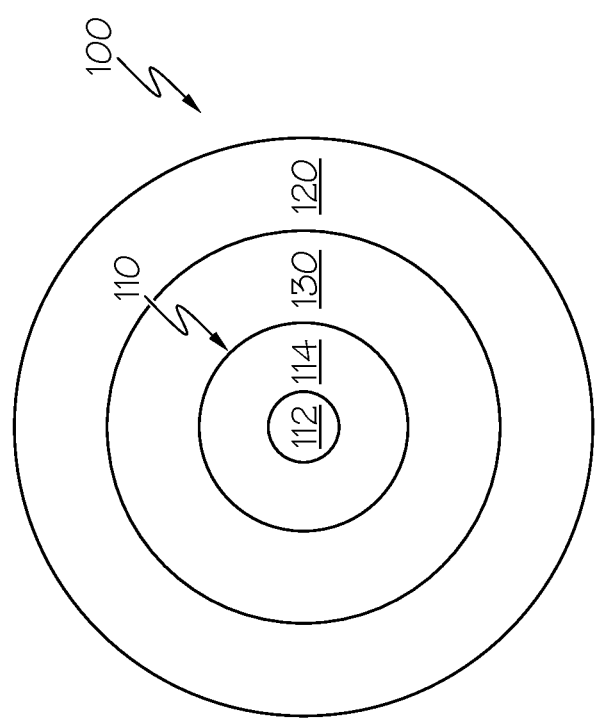
FIG. 1 schematically depicts a cross-sectional axial view of a coated optical fiber, according to one or more embodiments described herein.

Reference will now be made in detail to embodiments of methods and devices for measuring properties of coatings on optical fibers or optical fibers themselves, examples of which are illustrated in the accompanying drawings. Whenever possible, the same reference numerals will be used throughout the drawings to refer to the same or like parts. Generally, optical fiber coatings have mechanical properties suitable for protecting the optical fiber housed within According to one embodiment, Brillouin spectroscopy (sometimes referred to herein as "Brillouin shift analysis," or "Brillouin frequency shift analysis") can be utilized on optical fiber coatings to determine properties of the coatings. For example, Brillouin frequency shift analysis, as described herein, can be utilized to measure the Young's modulus of a coating on an optical fiber while the coated optical fiber is in motion, and without contacting the coated optical fiber.

While Brillouin frequency shift analysis is conventionally utilized only for measuring properties of transparent materials, the methods described herein allow for the measurement of mechanical properties of coatings even when those coatings are not non-transparent and even under other coatings. It has been found that equations that are applied to determine various mechanical properties of a transparent material based on its Brillouin frequency shift cannot be used to accurately compute the properties of a non-transparent material. In order to overcome the problem of Brillouin analysis on non-transparent materials, as described herein, sample Brillouin frequency shift data is collected from known material samples (with known mechanical properties). The sample data is used to develop a correlation between mechanical properties and Brillouin frequency shift, referred to herein as "correlation data." The correlation data is then used to determine the mechanical property of the coating by comparing the collected Brillouin data of the coating with the correlation data. Additionally, the methods described herein may allow for the measurement of properties of a coating while the coating is in motion and in a non-destructive means, allowing for real-time adjustment of processing parameters while the coated optical fiber is being produced.

Optical fibers, such as those made from glass, may be coated with one or more curable polymer coatings. These coatings may include a primary coating and a secondary coating, wherein the primary coating may generally be an inner coating having a relatively high degree of flexibility (i.e., low Young's modulus) utilized to cushion the optical fiber, and the secondary coating, disposed over the primary coating, may generally be relatively hard (i.e., high Young's modulus) in order to protect the underlying glass optical fiber. The primary coating, secondary coating, and/or optical fiber may be analyzed by Brillouin scattering techniques, as described herein, to measure their respective properties, such as, but not limited to, Young's modulus.

According to exemplary embodiments, an example of a coated optical fiber is shown in the schematic cross-sectional axial view in FIG. 1. The coated optical fiber 100 has a lateral direction extending in the major length of the coated optical fiber 100 and an axial direction having a substantially circular cross-section, as shown in FIG. 1. Coated optical fiber 100 includes an optical fiber 110 (including a core 112 and a cladding 114) surrounded by primary coating 130 and secondary coating 120. For example, as shown in FIG. 1, the primary coating 130 surrounds the optical fiber 110 and the secondary coating 120 surrounds the primary coating 130. In embodiments, the primary coating 130 may be in direct contact with the optical fiber 110 and the secondary coating 120 may be in direct contact with the primary coating 130. However, embodiments of coated optical fibers 100 containing interlayers positioned between the optical fiber 110 and the primary coating 130, and/or between the primary coating 130 and the secondary coating 120, are contemplated herein.

The optical fiber 110 may generally include a core 112 and a cladding 114. The core 112 and cladding 114 may comprise a wide variety of transparent materials, including glass, polymers, and the like. Generally, the core 112 and the cladding 114 are transparent materials where the cladding 114 has a lower refractive index than the core 112. The optical fiber 110 may be a single mode fiber, or a multimode fiber. The optical fiber 110 may be adapted for use as a data transmission fiber (e.g., SMF-28®, LEAF®, and METRO-COR®, each of which is available from Corning Incorporated of Corning, N.Y.). Alternatively, the optical fiber 110 may perform an amplification, dispersion compensation, or polarization maintenance function. It should be understood that that the coatings (i.e., primary coatings, secondary coatings) described herein are suitable for use with virtually any optical fiber for which protection from the environment is desired.

As depicted in FIG. 1, optical fiber 110 is surrounded by a primary coating 130. Primary coating 130 may comprise a polymer composition, such as a soft crosslinked polymer material having a low Young's modulus (e.g., less than about 5 MPa at 25° C.) and a low glass transition temperature (e.g., less than about −10° C.). The primary coating 130 may have a higher refractive index than the cladding 114 of the optical fiber 110 in order to allow it to strip errant optical signals away from the optical fiber core 112. The primary coating 130 should maintain adequate adhesion to the optical fiber 110 during thermal and hydrolytic aging, yet be strippable therefrom for splicing purposes. The primary coating 130 typically has a thickness in the range of 25-40 µm (e.g. about 32.5 µm). The primary coating 130 is typically applied to the glass fiber as a liquid and cured, as will be described in more detail hereinbelow. Example curable compositions used to form primary coatings may be formulated using an oligomer (e.g., a polyether urethane acrylate), one or more monomer diluents (e.g. ether-containing acrylates), a photoinitiator, and other additives (e.g., antioxidants).

In the embodiment of coated optical fiber 100, the primary coating 130 is surrounded by a secondary coating 120. The secondary coating 120 may be formed from a cured polymeric material, and may typically have a thickness in the range of 25-40 µm (e.g., about 32.5 µm). The secondary coating may have sufficient stiffness to protect the optical fiber; may be flexible enough to be handled, bent, or spooled; may have a relatively small tackiness to enable handling and prevent adjacent convolutions on a spool from sticking to one another; may be resistant to water and chemicals such as optical fiber cable filling compound; and may have adequate adhesion to the coating to which it is applied (e.g., the primary coating 130). Secondary coating compositions may include oligomers, monomers, and other additives. Generally, the material of the secondary coating 120 has a relatively high Young's modulus, such as greater than about 400 MPa, 600 MPa, 800 MPa, 1000 MPa, 1200 MPa, 1400 MPa, 1600 MPa, 1800 MPa, or even greater than about 2000 MPa. The coated optical fiber 100 may further comprise printing or coloring, such as an ink layer (not depicted in FIG. 1) deposited on at least a portion of the secondary coating 120.

Figure 2:
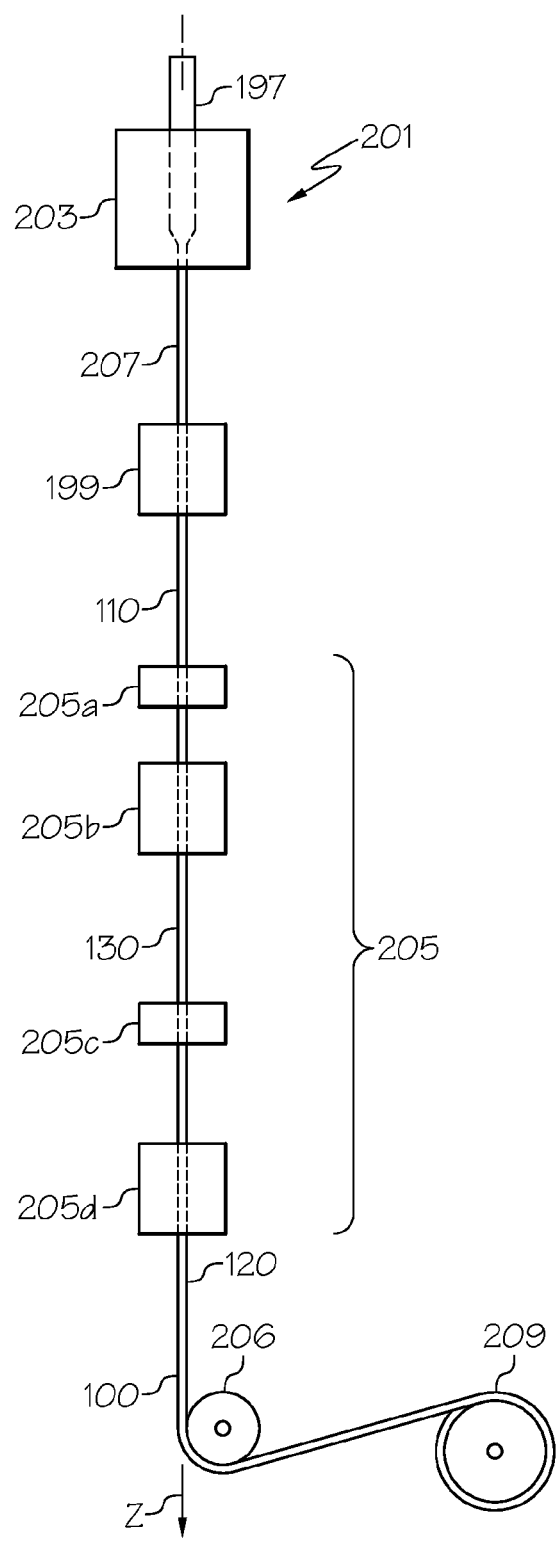
FIG. 2 schematically depicts a drawing apparatus showing an optical fiber being drawn and coated, according to one or more embodiments described herein.

Coated optical fibers may be produced by a drawing process, where the optical fiber is drawn, coatings are applied, and the coatings are cured while the optical fiber is in motion. Referring now to FIG. 2, a drawing device is depicted which may be used to produce a coated optical fiber 100. A preform 197 is melted within a drawing furnace 203 of a drawing tower 201. For example, the preform 197 may be heated to a temperature of at least about 2000° C. A glass fiber 207 is obtained that is cooled by the surrounding air and then in at least one cooling device 199 to set the optical fiber 110 at a suitable temperature for polymer coating The optical fiber 110 generally moves in the Z-direction, shown on FIG. 2. A coating device 205 operates to form one or more coatings on the optical fiber 110 from at least one coating resin that is usually cured by, for example, ultraviolet light. However, a variety of curing conditions may be utilized. The coating device 205 may include an injection device 205*a* which deposits the primary coating polymer (pre-cured) around the optical fiber 110, and a curing device 205*b* which cures the primary coating polymer to form the primary coating 130. Following application of the primary coating 130, a downstream injection device 205*c* may deposit the secondary coating polymer (pre-cured) around the primary coating 130 and optical fiber 110, and a curing device 205*d* may cure the secondary coating polymer to form the secondary coating 120. The resulting coated optical fiber 100 may be pulled by a capstan 206 and wound onto a spool 209.

Physical properties of coatings may be affected by processing conditions and coating material compositions. For example, cure processing conditions (e.g., time and/or intensity) of the curing steps may affect the physical properties, such as Young's modulus, of the coatings. Specifically, curing times and intensities may determine the degree of cure (i.e., the amount of cross linking or other curing, sometimes referred to herein as the "cure percentage") of the polymer, and the Young's modulus of a material composition may be a function of the degree of cure. Generally, the Young's modulus may be greater with increased curing degree, caused by higher intensity or longer time of cure. Therefore, measuring the physical properties of the coatings, such as the Young's modulus, may be an important step in determining whether the coated optical fibers 100 are suitable for use. For example, a measurement may be made to determine whether the Young's modulus of one or more of the coatings is within an acceptable range for commercial use. Then, if the Young's modulus is not within the determined acceptable range, a change can be made to the cure processing conditions, such as the intensity or time of radiation, to modify the cure percentage and change the mechanical properties of the coatings, e.g., to increased the Young's modulus.

Conventional techniques for measuring mechanical properties of coatings may be difficult, and may require offline testing (i.e., when the coated optical fiber is not being drawn and is not in motion) of portions of the coatings applied during drawing and coating. These conventional techniques require the fiber to be stopped and sometimes require actual destruction to the fiber for material sampling. As such, conventional testing techniques may not allow for testing of a coating's mechanical properties as the coated optical fiber is in motion during drawing. Therefore, with conventional methods, adjustments to processing conditions, such as curing conditions, cannot be made until the drawing process is halted and properties of the coatings are measured by conventional means offline.

In embodiments described herein, one or more properties of a coating on an optical fiber, such as a Young's Modulus, may be measured while the coated optical fiber is online (i.e., when the coated optical fiber is being drawn and in motion) by utilizing collected Brillouin scattering data. The measuring of the property may be conducted in an express manner and/or without physical contact with or physical damage to the coated optical fiber 100. Since the mechanical properties of the coatings can be measured during the drawing process (i.e., online) adjustments to the cure conditions can be made during the drawing process if necessary.

Generally, mechanical property data, such as a Young's modulus, of a coating on an optical fiber can be measured by collecting Brillouin frequency shift data of the coating on the optical fiber and determining the mechanical property of the coating by comparing the collected Brillouin frequency shift data of the coating with correlation data. Generally, correlation data may comprise data collected from known materials, such as Brillouin frequency shift data and mechanical data of materials with known curing degrees and compositions. In one embodiment, the correlation data may comprise a set of collected sample Brillouin frequency shift data of a plurality of sample materials and a set of collected sample mechanical property data of the plurality of sample materials. This may include Young's modulus data and Brillouin frequency shift data for a set of sample materials, where the sample materials have the same composition but have varying properties, such as Young's modulus, caused by varying cure degree.

Figure 3:
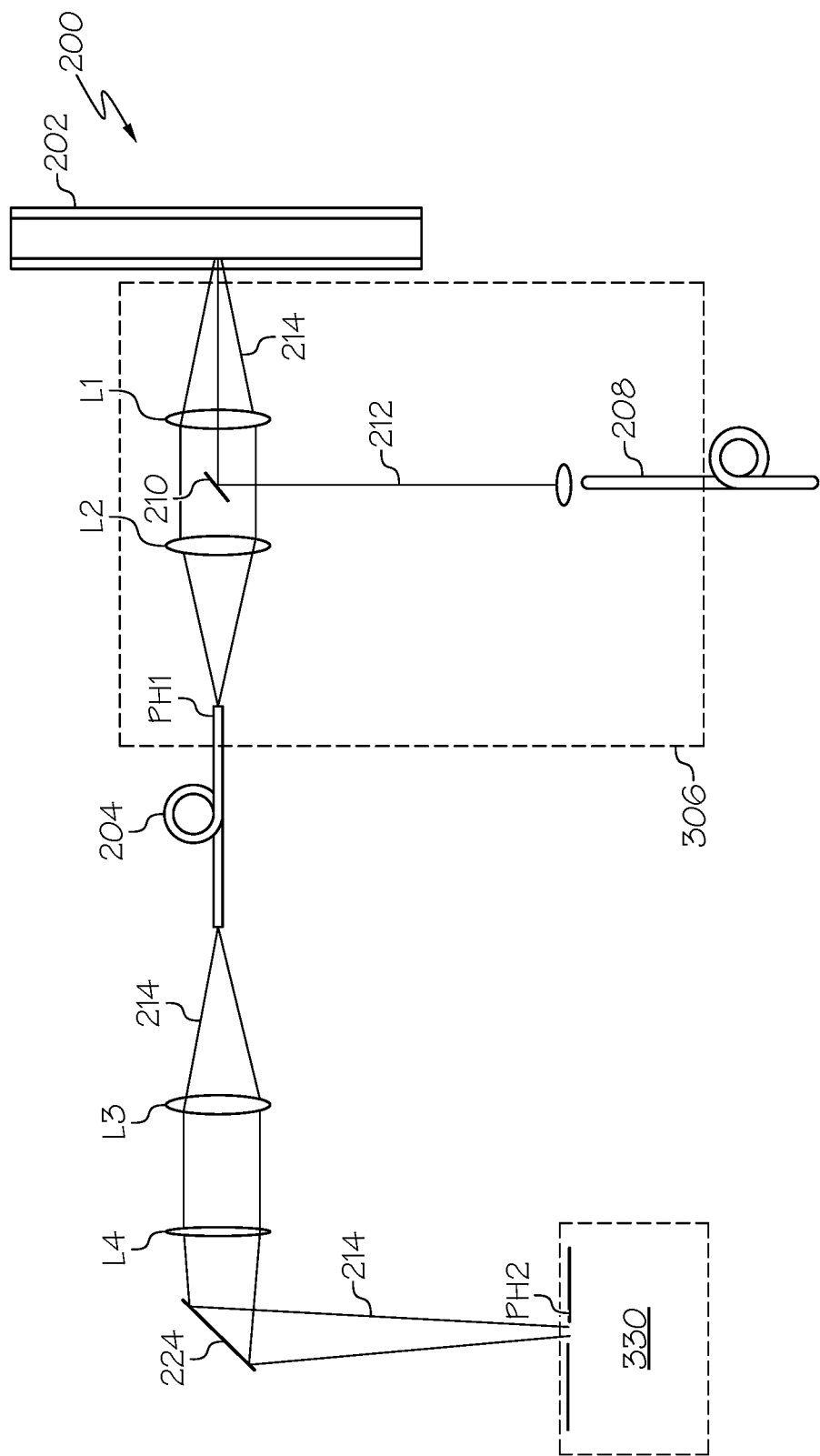
FIG. 3 schematically depicts a Brillouin spectrometer utilized to measure properties of coated optical fibers, according to one or more embodiments described herein.

Brillouin frequency shift data can be collected from a coated optical fiber or other sample material with a Brillouin spectrometer as depicted in the apparatus of FIG. 3. Referring to FIG. 3, a Brillouin spectrometer 200 may utilize a Fabry-Perrot interferometer 330, to measure a Brillouin frequency shift value of a test subject 202. The test subject 202, from which Brillouin data is collected, could be a variety of materials, such as the sample materials used to form the correlation data, or the coated optical fiber which is measured. The Fabry-Perrot interferometer 330 may be in proximity with the test subject 202 or may be positioned remotely, such as in another room. The test subject 202 may be motionless or may be in motion, such as coated optical fiber during the drawing process, while the Fabry-Perrot interferometer 330 is used to measure the Brillouin frequency shift of the material of the test subject 202.

For example, the Brillouin spectrometer may comprise a test module 306 and a Fabry-Perrot interferometer 330. A multi mode optical fiber 208 may, as a transmission optical fiber, deliver a laser 212 from a laser source (not shown) into the test module 306. The laser 212 may be reflected off a mirror 210 and into the test subject 202. The Brillouin scatter radiation 214 generated from the test subject 202 is collimated by a first lens L1 and directed into and through a first pinhole PH1 by a second lens L2 and into a transmission optical fiber such as multi mode optical fiber 204. The Brillouin scatter radiation 214 propagates through the multi mode optical fiber 204 and into a third lens L3 that collimates the Brillouin scatter radiation. Following propagation through a fourth lens L4, the Brillouin scatter radiation 214 may reflect off a mirror 224 and through a second pin hole PH2 and into the Fabry-Perrot interferometer 330.

As examples and not as limitations, the Fabry-Perrot interferometer 330 may have a sampling spot diameter of 100 μm, the pin hole PH2 may be 450 μm in size, and the pin hole PH1 may be about 100 μm in size. In embodiments, lens L1-L4 may have a focal distance in a range of from about 20 mm to about 25 mm. In embodiments, lens L1 may have a focal length in a range of from about 50 mm to about 150 mm, lens L2 and L3 may have a focal length F in a range of from about 98 mm to about 122 mm, and lens L4 may have a focal length F in a range of from about 300 mm to about 400 mm. In embodiments, the multi mode optical fiber 204 may have a core diameter of about 50.0 μm and numerical aperture ("NA") of about 0.2. While FIG. 3 depicts one embodiment of a Brillouin spectrometer 200, it should be understood that any Brillouin spectrometer capable of analyzing Brillouin scatter of a test subject could be utilized to collect Brillouin frequency shift data from the coated optical fiber.

Figure 4:
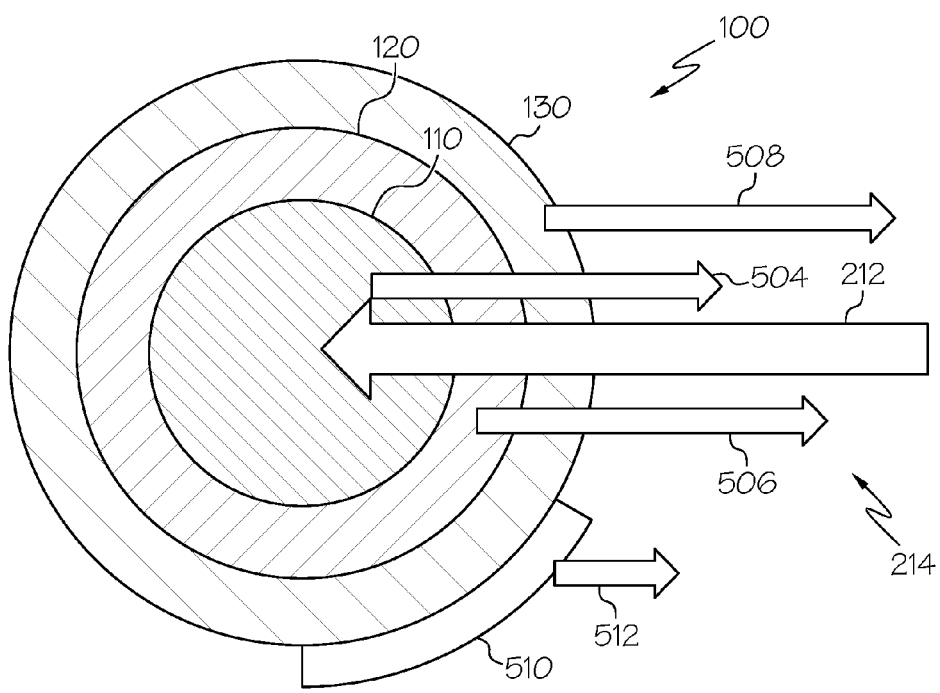
FIG. 4 schematically depicts a cross-sectional axial view of a coated optical fiber being analyzed by Brillouin spectroscopy, according to one or more embodiments described herein.

Referring to FIG. 4, a cross-sectional schematic view of a coated optical fiber 100 undergoing Brillouin analysis is schematically depicted. The laser 212 propagates into the coated optical fiber and Brillouin scatter radiation 214 is transmitted at least partially in a direction opposite the laser 212. The Brillouin scatter radiation 214 comprises radiation from each material of the coated optical fiber 100. For example, the Brillouin scatter radiation may comprise Brillouin scatter optical fiber radiation 504 from the optical fiber 110, primary coating radiation 506 from the primary coating 130, secondary coating radiation 508 from the secondary coating, and ink radiation 512 from an ink layer 512.

Figure 5:
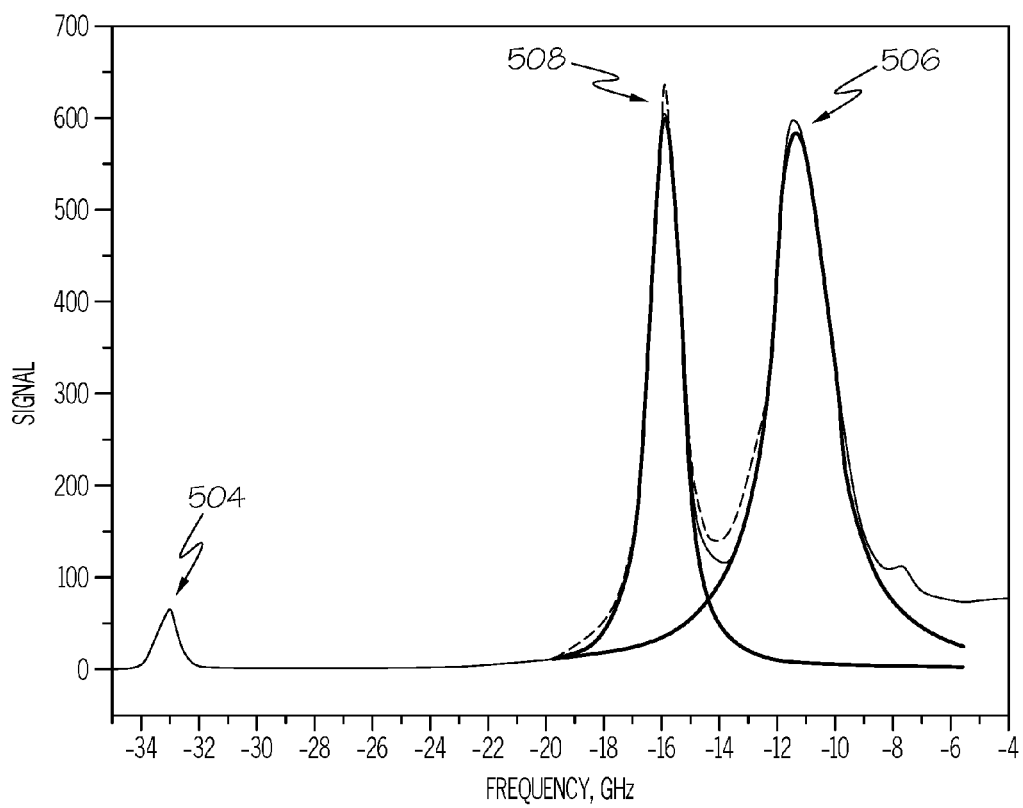
FIG. 5 graphically depicts an example plot of a Brillouin spectrum of a coated optical fiber, according to one or more embodiments described herein.

An example of Brillouin frequency shift data for a coated optical fiber is depicted in FIG. 5. The collected Brillouin frequency shift data of the coating may comprise a Brillouin frequency shift peak frequency for each material of the coating. For example, the Brillouin spectrum of FIG. 5 shows peaks at approximately −33 GHz, −16 GHz, and −11 GHz, which represent Brillouin frequency shift peaks representative of the optical fiber 110 (of its core and clad portions), secondary coating 120, and primary coating 130, respectively. FIG. 5 does not depict an ink peak, but such a peak is contemplated herein.

Each collected Brillouin frequency shift data peak, which relates to a specific coating or the core and clad portions, is compared with correlation data for that specific coating material. The correlation data may comprise a set of collected sample Brillouin frequency shift data of a plurality of sample materials and a set of collected sample mechanical property data of the plurality of sample materials. For example, for each material composition known to be a coating of the optical fiber, a plurality of sample materials having that composition (and varying cure degree) can be prepared and tested for a mechanical property (through mechanical means) and for Brillouin frequency shift (by Brillouin spectroscopy). Therein, in some embodiments, the coating on the optical fiber comprises a material composition that is substantially identical to the sample composition of the sample materials. It should be noted that each coating of the optical fiber is compared to separate correlation data produced from a like composition, and more than one set of correlation data is generally needed to evaluate multiple coatings on a single optical fiber which have different material compositions.

For example, to measure the Young's modulus of a secondary coating of a known composition, sample materials having the chemical composition of the secondary coating with varying cure degrees would be tested for their mechanical properties and for their Brillouin scatter. At least a portion of the sample materials are prepared with varying processing conditions (e.g., cure conditions) and, therefore, have different values of a mechanical property (e.g., Young's modulus). In one embodiment, the varying processing conditions may comprise varying cure conditions, and at least a portion of the sample materials may comprise different cure degrees. The measured mechanical property may be a function of the cure condition. For example, the Young's modulus of a coating material may be a function of the cure condition, so that materials with the same composition have different Young's modulus based on their respective cure degree.

Each sample material having the same composition and varying cure condition is analyzed by Brillouin analysis. This set of collected sample Brillouin frequency shift data of the plurality of sample materials may comprise a Brillouin frequency shift peak frequency for each sample material. The set of collected sample mechanical property data of the plurality of sample materials may comprise an experimentally determined Young's modulus for each sample material.

Figure 6:
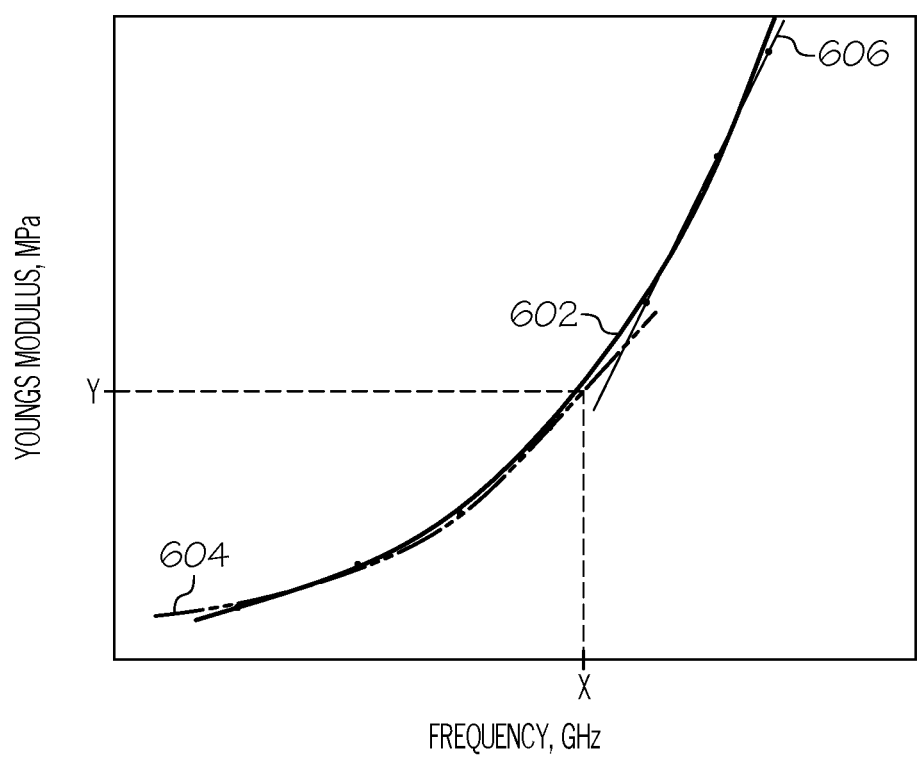
FIG. 6 graphically depicts an example of correlation data, according to one or more embodiments described herein.

Correlation data, which includes the set of collected sample Brillouin frequency shift data of a plurality of sample materials, and the set of collected sample mechanical property data of the plurality of sample materials, can be plotted such as shown in FIG. 6. FIG. 6 graphically depicts an example of peak frequency (x-axis) versus Young's modulus (y-axis) for a plurality of sample materials having the same composition and varying cure degree. The Young's modulus is measured by a tensile tester, and the frequency is determined by Brillouin frequency shift spectroscopy. Each data point of FIG. 6 represents a sample material with a different cure degree, and is plotted relative to its Brillouin frequency shift peak (the peak as shown in FIG. 5) and its Young's modulus (determined by tensile testing means). Without being bound by theory, Brilluoin frequency shift depends on wavelength of light used as excitation (i.e., a wavelength ($\lambda$) of 532 nm was used in the Examples described in greater detail below) and the geometry utilized in the experimental determination of frequency shift (i.e., a back scattering geometry as used in the Examples below in which an angle between excitation and scattering light wave-vectors is 180 degrees).

The speed of sound obtained from Brillouin frequency shift data may be expressed for a backscattering geometry as the following:

$$V_l = \Delta f \lambda / (2n) \qquad \text{Equation (1)}$$

In Equation (1), $V_l$ is a longitudinal speed of sound in the material, $\Delta f$ is a Brillouin frequency shift, and n is a refractive index of the material. For other geometries where the angle between excitation and scattering light wave-vectors is not 180 degrees (i.e., if the angle between excitation and scattering beams wavevectors is $\Theta$), the speed of sound may be expressed as the following:

$$V_l = \Delta f \lambda / (2n * \sin(\Theta/2)) \qquad \text{Equation (2)}$$

From Equations (1) and (2) is it can be determined that since the speed of sound is not changing in an isotropic material for different geometries and different wavelength of excitation light as in the Examples described in greater detail further below, different Brillouin frequency shift may be obtained for the same samples of geometry and wavelength of light. As far as these parameters are kept constant, one could use Brillouin frequency shift for describing mechanical properties of a material, such as where reference samples (correlation data) and fiber samples are measured with the same geometry and excitation wavelength.

The set of collected sample Brillouin frequency shift data may be correlated with the set of collected sample mechanical property data to determine a quantitative relationship therebetween. For example, the plot of FIG. 6 shows that the Brillouin frequency shift generally increases with higher Young's modulus. As used herein, a quantitative relationship refers to any relationship between the set of collected Brillouin frequency shift data of the plurality of sample materials and the set of collected sample mechanical property data of the plurality of sample materials that can be approximately expressed quantitatively. For example, a quantitative relationship is shown in FIG. 6 since a mathematical function can approximately express the data points of the plot. It should be understood the relationship need not be exactly expressed by a mathematical function, and for example, a least squares method may be utilized to determine a function for the empirical data.

A quantitative relationship between Young's modulus and frequency is shown in FIG. 6, where the data points approximately form an exponential curve 602. However, other quantitative relationships are contemplated herein, such as linear or other non-linear relationships. Additionally, a quantitative relationship, such as a linear or non-linear relationship, may be present in a segment of the correlation data. For example, the correlation data may comprise a linear correlation in a range of the correlation data, such as shown with respect to line 606. In another embodiment, the correlation data may comprise a non-linear correlation in a range of the correlation data, such as shown with respect to line 604. For example, line 606 may better approximate the relationship between the empirical data at higher Young's modulus values and line 604 may better approximate the relationship between the empirical data at lower Young's modulus.

The mechanical property of the coating may be determined by comparing the collected Brillouin frequency shift data of the coating with the correlation data. In one embodiment, the collected Brillouin frequency shift data of the coating may be compared with correlation data by interpolating or extrapolating the correlation data to determine the mechanical property of the coating based on the collected Brillouin frequency shift data of the coating. For example, referring to FIG. 6, a collected Brillouin frequency shift of "X", as shown in the plot, would correspond with a Young's modulus of "Y" for the coating, based on the mathematical relationship shown as line 602. If the Brillouin data collected from a coating of the optical fiber was X, the methods described herein indicate that its Young's modulus was approximately Y. The empirical data of the sample materials, the correlation data, is utilized to determine the mechanical property of the coating.

In embodiments, the coatings that are measured may be non-transparent. As used herein, "non-transparent" materials do not transmit at least about 50% of light for at least a portion of wavelengths in the visible spectrum. The empirical data of the sample materials contained in the correlation data is believed to be needed to determine mechanical properties of non-transparent materials. While Brillouin scattering via Brillouin frequency shift testing may be used to obtain mechanical properties of substantially transparent materials, conventionally it has not known to be effectively used with partially-transparent or non-transparent materials, such as some polymer coatings of optical fibers. Mechanical property determination based on Brillouin scattering data of non-transparent materials was believed to be immeasurable by known mechanical property equations, resulting in incorrect mechanical property values.

Generally, mechanical properties may be obtainable from Brillouin frequency shift testing if density of a transparent material and its refractive index are known. Brillouin scattering is based on an inelastic scattering of acoustic waves absorbed by materials, where the scattering on a shifted frequency carries information about a speed of sound of the materials. Speed of sound is linked to density and a Young's Modulus of a material. Different mechanical properties may be obtained such as shear modulus, bulk modulus, and Poisson ratio. For example, for transparent materials, a Brillouin frequency shift can be used to determine Young's modulus through the following Equation (3) for backscatter (Brillouin scattering) based geometry, where $C_{11}$ is an the Young's modulus, $\rho$ is density, $\lambda_0$ is a wavelength of light, $\Delta f$ is the Brillouin frequency shift, and n is a refractive index of a material, for measurements undertaken at backscatter geometry with an angle between excitation and scattering beams wave-vectors equal to 180°.

$$C_{11} = \rho((\lambda_0 \Delta f)/(2n))^2 \quad \text{Equation (3)}$$

However, knowing exact values for density and refractive index tends to be difficult as they may change as a result of a cure condition variation. Further, Brillouin scattering is conventionally not applied to test non-transparent media. Since such Brillouin frequency shift measurements occur at supersonic frequencies (i.e., GHz range), dispersion of Young's modulus is assumed to be weak, as is the case for transparent media such as glass or crystals. For example, in the plot of FIG. 5, a peak frequency of the glass fiber 504 is shown to have a relatively low intensity signal of less than a 100 and a peak frequency value at about −33 GHz. However, generally non-or-minimally transparent materials tend to have very strong dispersion and testing at supersonic frequencies (having a testing range of about 1 μm to about 10 μm) is greatly differentiated from testing with lower or static mechanical-based tests (having a test component length of about a few mm or cm). For example, in the plot of FIG. 3, peak frequencies of a primary polymer coating 506 and a secondary polymer coating 508 are shown to have a relatively high intensity signals of greater than 500 and respective low and intermediary peak frequency values at about −11 GHz and −16 GHz. Thus, the intermediary Brillouin frequency shift peak of the secondary coating 508 and the low Brillouin frequency shift peak of the primary coating 506 are spaced away by at least 10 GHz from the Brillouin frequency shift peak for the optical fiber 504. Utilizing such Brillouin frequency shift values in known equations conventionally result in Young's Modulus values of ineffective and incorrect ranges, such as resulting in GPa values where MPa values are desirable for effective fiber performance determinations.

For example, absolute values obtained by Brillouin spectroscopy (tested at a GHz frequency) for polymer materials have conventionally been much higher than those measured by resonance acoustics (tested in a kHz frequency range) or by way of static testing (tested at zero frequency) due to a very strong dispersion variation of mechanical properties of generally non-or-minimally transparent polymers with higher frequency testing. For example, a conventionally tested Poly(methyl methacrylate), or PMMA, thermoplastic material may have a PPMA bulk modulus at a few GPa range, for example, while in a static test it results in about a 1 GPa range.

EXAMPLES

Example #1

Figure 7:
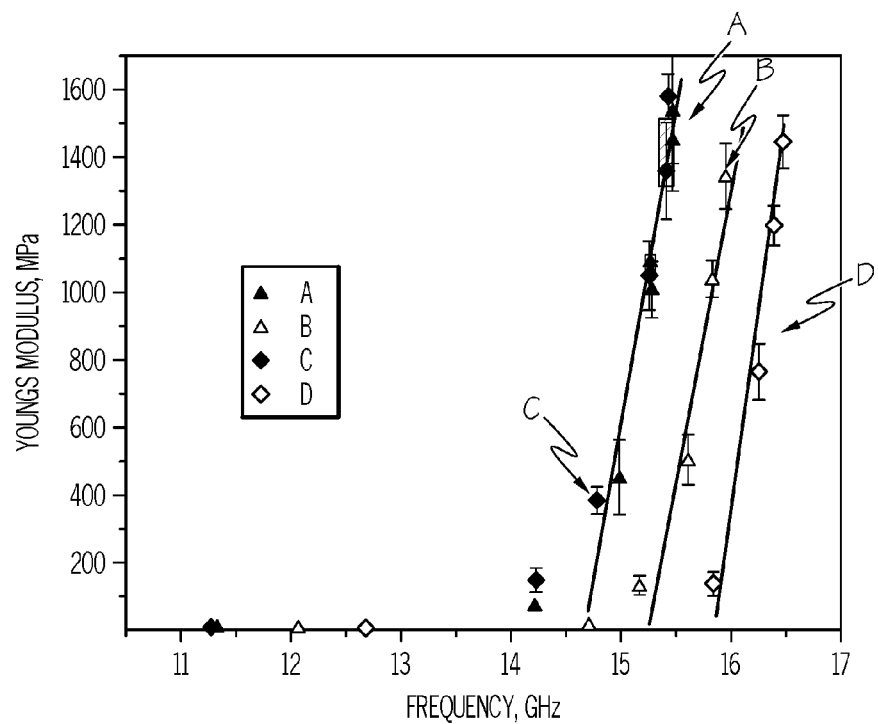
FIG. 7 graphically depicts experimentally derived correlation data, according to one or more embodiments described herein.
Figure 8:
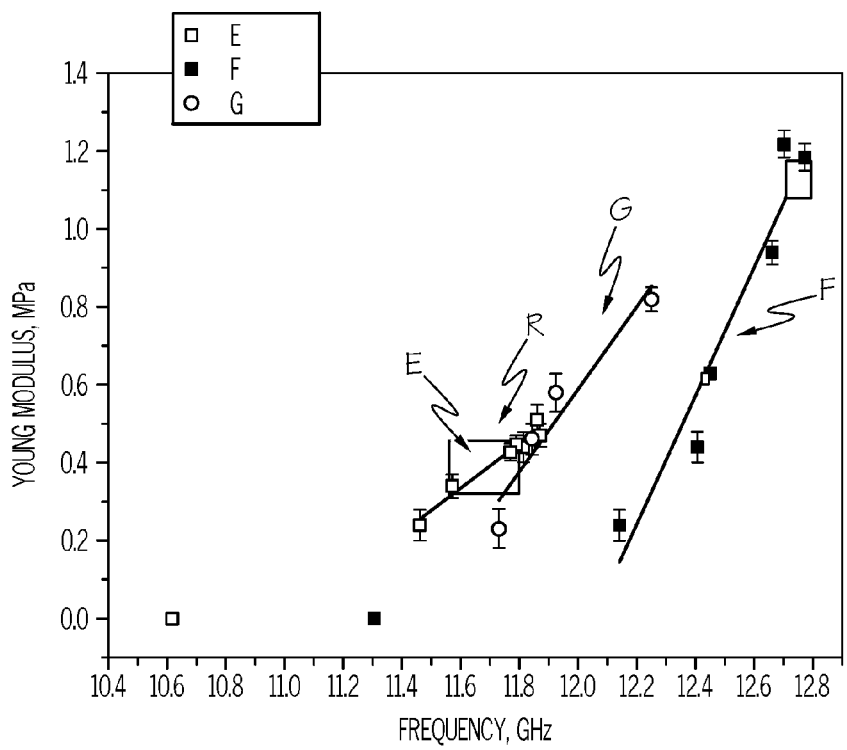
FIG. 8 graphically depicts experimentally derived correlation data, according to one or more embodiments described herein.

Referring to FIG. 7, a plurality of sample materials for secondary polymer coatings A, B, C, and D were tested to collect reference data Young's Modulus values and Brillouin frequency shift measurements, which were plotted against one another to show a correlation. The sample materials were cured for varying times to get a range of Young's modulus for each sample material. Referring to FIG. 8, a plurality of sample materials for primary polymer coatings E, F, and G were tested to collect reference data Young's modulus values and Brillouin frequency shift measurements, which were then corrected to one another. It was found that at high cure conditions, a substantially linear relationship would result between the static Young's modulus values and Brillouin peak shift frequencies, as shown in FIGS. 7 and 8. At varying cure conditions (such as from liquid to fully cured), a linear fit was found for a logarithmic or exponential scale conversion of Young's Modulus charted against frequency shift values.

Referring to FIG. 7, sample materials A, B, C, and D were tested and information about their respective mechanical properties and Brillouin frequency shift was correlated, where the sample materials A, B, C, and D were secondary coatings disposed about and contacting a primary coating that was disposed about and contacting an optical fiber. The sample materials were cured for varying times to get a range of Young's modulus for each sample material. Material A was a coating made of one commercially available coating composition (composition A'). Material B was a coating made of a CORNING® CPC6i composition. Material C was a coating made from another commercially available coating composition (composition C'). And material D was a coating made CORNING® CPCs1 composition as described in U.S. Patent App. Publ. No. 2014/0308015, entitled Single-Mode Fiber and Production Method Thereof, filed Jul. 20, 2010, the entirety of which is incorporated by reference herein. Varying draw conditions included testing material that had been drawn at a rate in a range of from about 10 m/s to about 20 m/s. Further, where an abbreviation of the form "n×m" means that n curing lamps were used for a primary coating and m curing lamps were used for a secondary coating at the draw process, lamp conditions included 1×2, 3×4, and 2×2 lamps for respective primary coating versus secondary coating testing.

Referring to FIG. 8, a plurality of sample materials E, F, and G were tested and information about their respective mechanical properties and Brillouin frequency shift was correlated, where the sample materials E, F, and G were primary coatings. Material E was a coating made of CORNING® CPCs1 composition. Material F was a coating made of a composition C'. And material G was a coating made of a CORNING® CPC6i composition as described in European Patent App. Publ. No. 2479156, entitled Radiation Curable Supercoatings for Single-Mode Optical Fiber, filed Oct. 8, 2010, the entirety of which is incorporated by reference herein.

Figure 9:
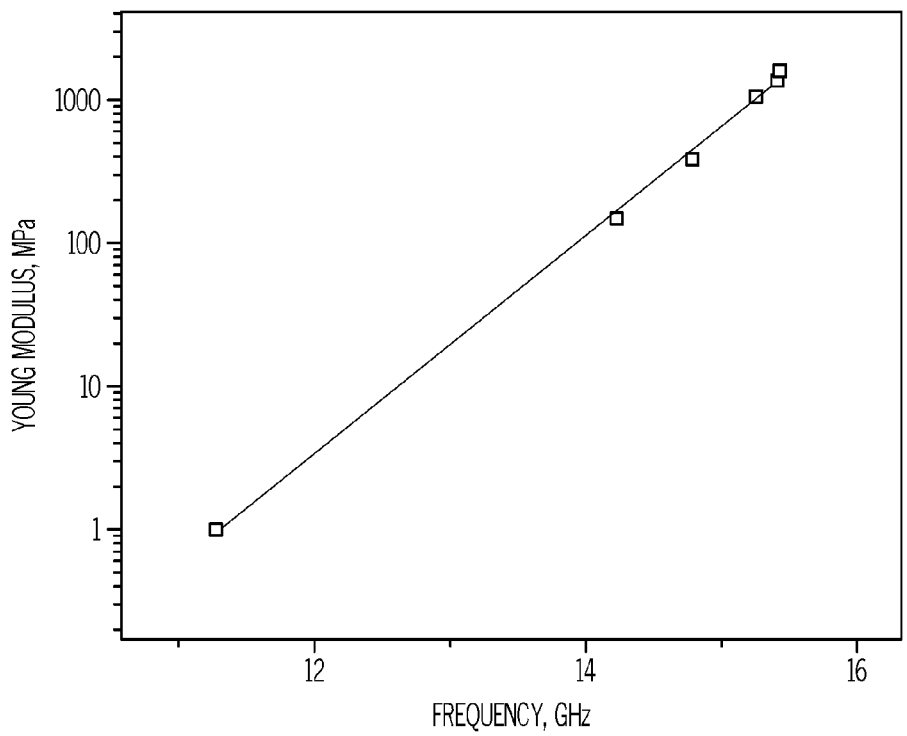
FIG. 9 graphically depicts an experimentally derived correlation data of FIG. 7 on a log scale, according to one or more embodiments described herein.
Figure 10:
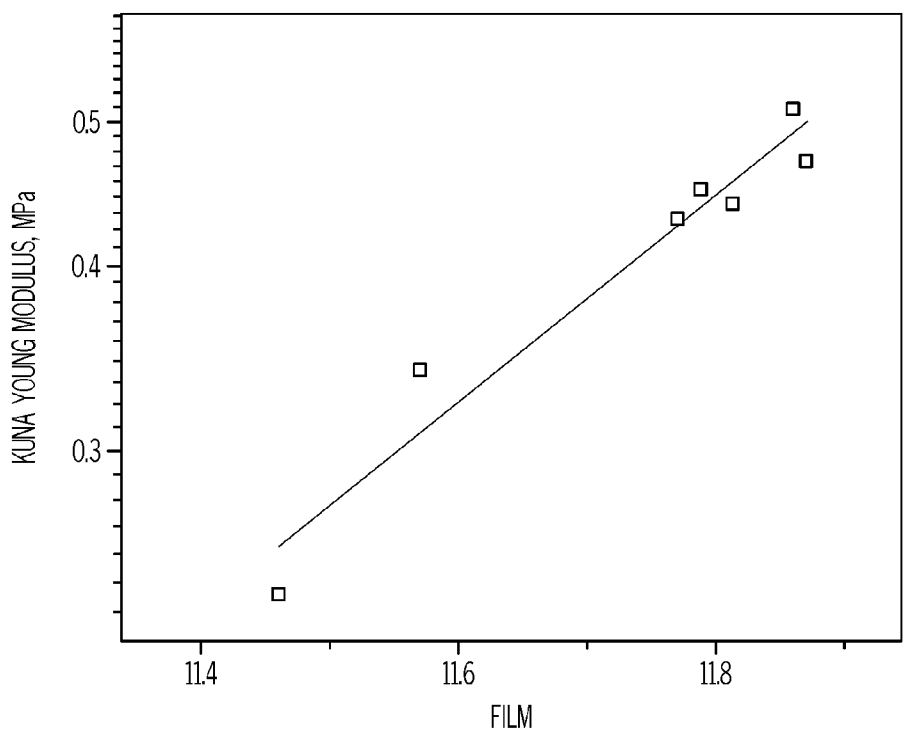
FIG. 10 graphically depicts an experimentally derived correlation data of FIG. 8 on a log scale, according to one or more embodiments described herein.

Furthermore, it was found that exponential relationships could be plotted for each sample material. For example, FIG. 9 is a log plot of sample material C, and FIG. 10 is a log plot of sample material F.

Example #2

As an example, another Corning coating material (material H) was tested at a draw rate of 30 m/s with 5×5 lamp conditions such that there were 5 curing lamps for the primary coating and 5 curing lamps for the secondary coating. A primary coating peak frequency of 11.804 GHz was measured, and a secondary coating peak frequency of 16.45 GHz was measured with an error of 0.02. The primary coating peak frequency value was compared against correlation data such as, for example, material E of the FIG. 8 reference chart to obtain a Young's Modulus value of 0.48 MPa with a recorded error of 0.045 MPa. The secondary coating peak frequency value was compared against correlation data such as, for example, material D of the FIG. 7 reference to obtain a Young's Modulus value of 1300 MPa with a recorded error of about 40 MPa. Excitation light used was at 532 nm, and geometry of experiment used back scattering geometry, where an angle between excitation and scattering light wave-vectors is 180 degrees.

Example #3

As an example, coating material H was tested at a draw rate of 42 m/s with 3×5 lamp conditions. A primary coating peak frequency of 11.81 GHz was measured, and a secondary coating peak frequency of 16.4 GHz was measured with an error of 0.06. The primary coating peak frequency value was compared against correlation data to obtain a Young's Modulus value of 0.4 MPa with a recorded error of 0.06 MPa. The secondary coating peak frequency value was compared against correlation data to obtain a Young's Modulus value of 1200 MPa with a recorded error of about 120 MPa. Excitation light used was at 532 nm, and geometry of experiment used back scattering geometry, where an angle between excitation and scattering light wave-vectors is 180 degrees.

Example #4

As an example, a coating material C was tested with 5×5 lamp conditions. A primary coating peak frequency of 12.59 GHz was measured, and a secondary coating peak frequency of 15.208 GHz was measured with an error of 0.071. The primary coating peak frequency value was compared against correlation data to obtain a Young's Modulus value of 0.9 MPa with a recorded error of 0.045 MPa. The secondary coating peak frequency value was compared against correlation data to obtain a Young's Modulus value of 1050 MPa with a recorded error of about 142 MPa. Excitation light used was at 532 nm, and geometry of experiment used back scattering geometry, where an angle between excitation and scattering light wave-vectors is 180 degrees.

Example #5

As an example, coating material C was tested with low cure 3×5 lamp conditions. A primary coating peak frequency of 12.58 GHz was measured, and a secondary coating peak frequency of 15.28 GHz was measured with an error of 0.06. The primary coating peak frequency value was compared against correlation data to obtain a Young's Modulus value of 0.9 MPa with a recorded error of 0.05 MPa. The secondary coating peak frequency value was compared against correlation data to obtain a Young's Modulus value of 1150 MPa with a recorded error of about 120 MPa. Excitation light used was at 532 nm, and geometry of experiment used back scattering geometry, where an angle between excitation and scattering light wave-vectors is 180 degrees.

Example #6

As an example, coating material C was tested with 1×2 lamp conditions and at a draw rate of 10 m/s. A primary coating peak frequency of 12.7 GHz was measured, and a secondary coating peak frequency of 15.44 GHz was measured with an error of 0.04. The primary coating peak frequency value was compared against correlation data to obtain a Young's Modulus value of 1.08 MPa with a recorded error of 0.05 MPa. The secondary coating peak frequency value was compared against correlation data to obtain a Young's Modulus value of 1200 MPa. Excitation light used was at 532 nm, and geometry of experiment used back scattering geometry, where an angle between excitation and scattering light wave-vectors is 180 degrees.

Example #7

As an example, coating material C was tested with 3×4 lamp conditions and at a draw rate of 20 m/s. A primary coating peak frequency of 12.77 GHz was measured, and a secondary coating peak frequency of 15.48 GHz was measured with an error of 0.01. The primary coating peak frequency value was compared against correlation data to obtain a Young's Modulus value of 1.2 MPa with a recorded error of 0.05 MPa. The secondary coating peak frequency value was compared against correlation data to obtain a Young's Modulus value of 1300 MPa. Excitation light used was at 532 nm, and geometry of experiment used back scattering geometry, where an angle between excitation and scattering light wave-vectors is 180 degrees.

Example #8

As an example, coating material C was tested with 2×2 lamp conditions and at a draw rate of 14 m/s. A primary coating peak frequency of 12.75 GHz was measured, and a secondary coating peak frequency of 15.45 GHz was measured with an error of 0.002. The primary coating peak frequency value was compared against correlation data to obtain a Young's Modulus value of 0.9 MPa with a recorded error of 0.05 MPa. The secondary coating peak frequency value was compared against correlation data to obtain a Young's Modulus value of 1250 MPa. Excitation light used was at 532 nm, and geometry of experiment used back scattering geometry, where an angle between excitation and scattering light wave-vectors is 180 degrees.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method for measuring a mechanical property of a coating on an optical fiber, the method comprising:
    collecting Brillouin frequency shift data of the coating on the optical fiber; and
    determining the mechanical property of the coating by comparing the collected Brillouin frequency shift data of the coating with correlation data, wherein the correlation data comprises:
    a set of collected sample Brillouin frequency shift data of a plurality of sample materials; and
    a set of collected sample mechanical property data of the plurality of sample materials, wherein:
    each of the sample materials comprises a substantially identical sample composition comprising one or more curable polymers;
    at least a portion of the sample materials are prepared with varying processing conditions and have different values of the mechanical property;
    the coating on the optical fiber comprises a material composition that is substantially identical to the sample composition of the sample materials; and
    the set of collected sample Brillouin frequency shift data is correlated with the set of collected sample mechanical property data to determine a quantitative relationship therebetween.

2. The method of claim 1, wherein a speed of sound value is obtained from the collected Brillouin frequency shift data at a backscattering geometry of experiment.

3. The method of claim 1, wherein collecting Brillouin frequency shift data of the coating on the optical fiber occurs while the coated optical fiber is in motion.

4. The method of claim 1, wherein the varying processing conditions comprise varying cure conditions and at least a portion of the sample materials comprise different cure degrees, and wherein the measured mechanical property is a function of the cure condition.

5. The method of claim 1, wherein the coating is a primary coating contacting at least a portion of the optical fiber, the primary coating comprising a Young's Modulus of less than about 5 MPa.

6. The method of claim 1, wherein the coating is a secondary coating comprises a Young's Modulus of at least greater than 1000 MPa, wherein the secondary coating is not in direct contact with the optical fiber.

7. The method of claim 1, wherein the measured mechanical property is a Young's Modulus.

8. The method of claim 1, wherein the coating is non-transparent by not transmitting at least about 50% of light for at least a portion of wavelengths in the visible spectrum.

9. The method of claim 1, wherein the coating is a tertiary coating comprising an ink layer.

10. The method of claim 1, wherein the correlation data comprises a linear correlation in a range of the correlation data.

11. The method of claim 1, wherein the correlation data comprises a non-linear correlation in a range of the correlation data.

12. The method of claim 1, wherein:
    the correlation data comprises a linear correlation in a first range of the correlation data;
    the correlation data comprise a non-linear correlation in a second range of the correlation data; and
    the first range is greater than the second range in terms of mechanical property data.

13. The method of claim 1, wherein Brillouin frequency shift data is collected by a Brillouin frequency shift data collector comprising a Fabry-Perrot interferometer.

14. The method of claim 13, wherein the Brillouin frequency shift data collector is remotely positioned at a distance away from the coated optical fiber, and wherein one or more lens units and one or more transmission optical fibers are positioned between the Brillouin frequency shift data collector and the coated optical fiber.

15. The method of claim 1, wherein the collected Brillouin frequency shift data of the coating comprises a Brillouin frequency shift peak frequency of a material of the coating.

16. The method of claim 1, wherein the set of collected sample Brillouin frequency shift data of the plurality of sample materials comprises a Brillouin frequency shift peak frequency for each sample material.

17. The method of claim 1, wherein the set of collected sample mechanical property data of the plurality of sample materials comprises an experimentally determined Young's modulus for each sample material.

18. The method of claim 1, wherein comparing the collected Brillouin frequency shift data of the coating with correlation data comprises interpolating or extrapolating the correlation data to determine the mechanical property of the coating based on the collected Brillouin frequency shift data of the coating.

19. A method for measuring a Young's modulus of a coating on an optical fiber, the method comprising:
    collecting Brillouin frequency shift data of the coating on the optical fiber; and determining the Young's modulus of the coating by comparing the collected Brillouin frequency shift data of the coating with correlation data, wherein the correlation data comprises:
- a set of collected sample Brillouin frequency shift data of a plurality of sample materials; and
- a set of collected sample Young's modulus data of the plurality of sample materials, wherein:
- each of the sample materials comprises a substantially identical sample composition comprising one or more curable polymers;
- at least a portion of the sample materials are prepared with varying cure conditions and have different values of Young's modulus;
- the coating on the optical fiber comprises a material composition that is substantially identical to the sample composition of the sample materials; and
- the set of collected sample Brillouin frequency shift data is correlated with the set of collected sample Young's modulus data to determine a quantitative relationship therebetween.

20. The method of claim 19, wherein the coating is non-transparent by not transmitting at least about 50% of light for at least a portion of wavelengths in the visible spectrum, and wherein collecting Brillouin frequency shift data of the coating on the optical fiber occurs while the coated optical fiber is in motion.

* * * * *

UNITED STATES PATENT AND TRADEMARK OFFICE
CERTIFICATE OF CORRECTION

| | |
|---|---|
| PATENT NO. | : 10,197,471 B2 |
| APPLICATION NO. | : 15/271572 |
| DATED | : February 5, 2019 |
| INVENTOR(S) | : Stephan Lvovich Logunov et al. |

It is certified that error appears in the above-identified patent and that said Letters Patent is hereby corrected as shown below:

On the Title Page

On page 2, Column 2, item (56), other publications, Line 2, delete "Propoerties" and insert -- Properties --, therefor.

In the Claims

In Column 14, Line 39, Claim 13, delete "Fabry-Perrot" and insert -- Fabry-Perot --, therefor.

Signed and Sealed this
Third Day of September, 2019

Andrei Iancu
*Director of the United States Patent and Trademark Office*